United States Patent [19]

Chang et al.

[11] 4,231,955
[45] Nov. 4, 1980

[54] SYNTHESIS OF ALKYL AND ALKYLAMINONITRILES

[75] Inventors: Clarence D. Chang, Princeton; William H. Lang, Pennington, both of N.J.; Rene B. LaPierre, Morrisville, Pa.

[73] Assignee: Mobil Oil Corporation, New York, N.Y.

[21] Appl. No.: 57,547

[22] Filed: Jul. 13, 1979

[51] Int. Cl.$^3$ ............... C07C 120/00; C07C 121/43; C07C 121/16; C07C 121/18
[52] U.S. Cl. ........................ 260/465.1; 260/465.5R
[58] Field of Search ............... 260/465.1, 465.5 R

[56] References Cited
U.S. PATENT DOCUMENTS

| 2,807,618 | 9/1957 | Cislak et al. | 546/348 X |
| 4,158,024 | 6/1979 | Kaeding et al. | 585/467 |
| 4,159,282 | 6/1979 | Olson et al. | 585/481 |
| 4,163,028 | 7/1979 | Tabak et al. | 585/486 X |

OTHER PUBLICATIONS

Advances in Catalysis, vol. 18, 1968, pp. 344-345.
Yasuda, et al., C.A., 82, 1975, 72793b.
Cislak, et al., C.A., 68, 1968, 105012n.
Grigoleit, et al., C.A., 79, 1973, 136985p.

Primary Examiner—Joseph Paul Brust
Attorney, Agent, or Firm—Charles A. Huggett; Raymond W. Barclay

[57] ABSTRACT

A method is provided for synthesizing alkylnitriles and alkylaminonitriles by reacting formaldehyde, a $C_1-C_5$ monohydric alcohol and a compound having the formula $R_1R_2NH$ where $R_1$ and $R_2$ are selected from the group consisting of hydrogen and alkyl groups containing 1 to 5 carbon atoms under effective conditions in the presence of a catalyst comprising a crystalline aluminosilicate zeolite having a silica to alumina ratio of at least about 12 and a constraint index within the approximate range of 1 to 12 and recovering from the resulting reaction mixture, a product containing at least one of the above nitrile compounds.

13 Claims, No Drawings

SYNTHESIS OF ALKYL AND ALKYLAMINONITRILES

BACKGROUND OF THE INVENTION

1. Field of the Invention

This invention relates to a method for synthesizing alkylnitriles and alkylaminonitriles by reaction of formaldehyde, a $C_1$–$C_5$ monohydric alcohol and a compound having the formula $R_1R_2NH$ where $R_1$ and $R_2$ are selected from the group consisting of hydrogen and alkyl groups containing 1 to 5 carbon atoms in the presence of a crystalline aluminosilicate zeolite, characterized by a silica to alumina ratio of at least about 12 and a constraint index, hereinafter defined, in the approximate range of 1 to 12.

2. Description of the Prior Art

It has heretofore been known to react acetaldehyde and ammonia either in the absence or presence of methanol and/or formaldehyde to yield pyridine and alkyl derivatives thereof. Such reaction has been carried out, as described, for example, in U.S. Pat. No. 2,807,618 in the presence of amorphous silica-alumina composites containing various promoters. Alkylpyridines have also been synthesized, as reported in Advances in Catalysis, Volume 18, page 344 (1968) Academic Press, Inc., New York N.Y. by passing gaseous acetaldehyde and ammonia over crystalline aluminosilicates, NaX and H-mordenite. Insofar as is known, formaldehyde, a $C_1$–$C_5$ monohydric alcohol, e.g., methanol, and a compound $R_1R_2NH$ where $R_1$ and $R_2$ have the above significance, e.g. ammonia have not heretofore been reacted in the presence of a crystalline aluminosilicate zeolite as described herein.

SUMMARY OF THE INVENTION

In accordance with the present invention, there is provided a method for synthesizing alkylnitriles and alkylaminonitriles by reacting formaldehyde, a $C_1$–$C_5$ monohydric alcohol and a compound having the formula $R_1R_2NH$ where $R_1$ and $R_2$ are selected from the group consisting of hydrogen and alkyl groups containing 1 to 5 carbon atoms in the presence of a catalyst comprising a particularly defined class of crystalline aluminosilicates which have been found to afford substantial yields of the desired nitrile products, useful as solvents and as intermediates for surfactants, agricultural chemicals and pharmaceutical synthesis.

The crystalline aluminosilicate zeolites employed as catalysts in the present synthesis method are those having a silica to alumina ratio of at least about 12 and a constraint index within the approximate range of 1 to 12. Typical of the zeolites used herein are ZSM-5, ZSM-11, ZSM-12, ZSM-35 and ZSM-38.

Reaction between formaldehyde, a $C_1$–$C_5$ alcohol and a compound having the formula $R_1R_2NH$ where $R_1$ and $R_2$ are selected from the group consisting of hydrogen and alkyl groups containing 1 to 5 carbon atoms and utilizing the above zeolites as catalysts is effectively carried out at a temperature between about 500° F. and about 1200° F. and preferably between about 700° F. and about 1000° F. at a pressure between about 1 atmosphere and about 100 atmospheres utilizing a liquid hourly space velocity of between about 0.2 and about 20 preferably between about 0.5 and about 10.

The mole ratio of formaldehyde, $C_1$–$C_5$ alcohol and $R_1R_2NH$ compound will generally be within the range defined by the following relationships:

$$1 \leq \frac{HCHO}{C_1\text{–}C_5 \text{ Alcohol}} \leq 5$$

$$1 \leq \frac{C_1\text{–}C_5 \text{ Alcohol}}{R_1R_2NH} \leq 10$$

and preferably by the relationships:

$$1 \leq \frac{H_2CHO}{C_1\text{–}C_5 \text{ Alcohol}} \leq 2$$

$$1 \leq \frac{C_1\text{–}C_5 \text{ Alcohol}}{R_1R_2NH} \leq 5$$

At the completion of the reaction, the product may be separated into its desired component by any feasible means, e.g., by fractionation, to recover a product containing at least one of the desired nitrile compounds, i.e., an alkylnitrile and/or an alkylaminonitrile.

DESCRIPTION OF SPECIFIC EMBODIMENTS

Representative of the $C_1$–$C_5$ monohydric alcohol reactants which may be utilized in the method of the present invention are methanol, ethanol, propanol, isopropanol, 1-butanol, 2-butanol, 1-pentanol, 2-pentanol and 3-pentanol, 2methyl-2-butanol, 3-methyl-3-butanol, 2-methyl-1-butanol, 3-methyl-1-butanol and 2-methyl-2-propanol.

Typical of the $R_1R_2NH$ compounds which may be used as reactants in the method of the present invention are those in which $R_1$ and $R_2$ are either both or individually hydrogen, methyl, ethyl, propyl, isopropyl, butyl, pentyl, isobutyl or isopentyl, including, for example, ammonia, dimethyl amine, diethyl amine, methyl ethyl amine, dipropyl amine, dibutyl amine, propyl butyl amine, propyl ethyl amine, propyl methyl amine, isobutyl isopropyl amine, isopropyl methyl amine, isopropyl ethyl amine, pentyl amine, isopentyl amine, methyl amine, ethylamine, methyl pentyl amine, ethyl pentyl amine, methyl isopentyl amine, ethyl isopentyl amine, etc.

The catalyst used in the method described herein comprises a crystalline aluminosilicate zeolite which is a member of a novel class of zeolites exhibiting some unusual properties. These zeolites induce profound transformation of aliphatic hydrocarbons to aromatic hydrocarbons in commercially desirable yields and are generally highly effective in conversion reactions involving aromatic hydrocarbons. Although they have unusually low alumina contents, e.i., high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, e.g., of the X and A type.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrainted access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocabons is passed at a 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| Clinoptilolite | 3.4 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination; with probability, in some instances, of compounding variable extremes.

While the above experimental procedure will enable one to achieve the desired overall conversion of 10 to 60% for most catalyst samples and represents prefered conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35 and ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which is incorporated herein by reference.

ZSM-12 is more particularly described in U.S. Pat. No. 3,832,449, the entire contents of which is incorporated herein by reference.

ZSM-35 is more particularly described in U.S. Pat. No. 4,016,245, the entire contents of which is incorporated herein by reference.

ZSM-38 is more particularly described in U.S. Pat. No. 4,046,859, the entire contents of which is incorporated herein by reference.

The specific zeolites described, when prepared in the presence of organic cations, are catalyticaly inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cation in the forming solution may not be absolutely essential to the formation of this type zeolite, however, the presence of these cations does appear to favor the formation of this special type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicate ae ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index, as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 100 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relative small amount of free space within the crystal, which might be expected to result in more stable structures. This free space, however, is important as the locus of catalytic activity.

Crystal framework densities of some typical zeolites are:

| Zeolite | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |

-continued

| Zeolite | Void Volume | Framework Density |
| --- | --- | --- |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelnite | .44 | 1.46 |
| Chabazite | .47 | 1.45 |
| A | .5 | 1.3 |
| Y | .48 | 1.27 |

The crystal size of the synthesized zeolite is generally within the approximate range of 0.01 to 40 microns.

When synthesized in the alkali metal form, the zeolite is conveniently converted to the hydrogen form, generally by intermediate formation of the ammonium form as a result of ammonium ion exchange and calcination of ammonium form to yield the hydrogen form. In addition to the hydrogen form, other forms of the zeolite wherein the orginal alkali metal has been reduced to less than about 1.5 percent by weight may be used. Thus, the original alkali metal of the zeolite or introduced hydrogen cations may be replaced by ion exchange with other suitable ions of Groups IB to VIII of the Periodic Table, including, by way of example, nickel, cadmium, copper, zinc, palladium, calcium or rare earth metals.

In practicing the desired synthesis method, it may be desirable to incorporate the above-described crystalline aluminosilicate zeolite in another material resistant to the temperature and other conditions employed in the process. Such matrix materials including synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays, which can be composited with the zeolite include those of the montmorillonite and kaolin families, which families including the sub-bentonites and the kaolins commonly known as Dixie, McNamee-Georgia and Florida clays or others in which the main mineral constituent is halloysite, kaolinite, dickite, nacrite or anauxite. Such clays can be used in a raw state as orginally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The following examples will serve to illustrate the method of the invention without limiting the same:

EXAMPLE 1

Formaldehyde (43.0 grams), methanol (30.6 grams) and ammonia (16.3 grams) were mixed with water (10.1 grams) and reacted over HZSM-5 at a temperature of 850° F., a pressure of 1 atmosphere at a liquid hourly space velocity of 1. Conversion (HCHO+CH$_3$OH) was 37.4 percent.

The product contained approximately 29% alkylnitriles and 45% alkylaminonitriles. Dimethylether and methylamines were also produced and may be recycled. Detailed product distribution is shown in the following table:

TABLE I

| Products, wt. %$^a$ | |
|---|---|
| H$_2$,CO, CO$_2$ | 4.5 |
| Dimethylether | 0.4 |
| Hydrocarbons | 3.7 |
| Methylamines | 18.0 |
| CH$_3$CN | 28.4 |
| CH$_3$CH$_2$CN | 0.8 |
| CH$_3$NHCH$_2$CN | 6.1 |
| CH$_3$NH CH$_2$CH$_2$CN | 2.2 |
| (CH$_3$)$_2$NCH$_2$CN | 18.1 |
| Unidentified Compounds | 17.8 |
| | 100.0 |

$^a$Normalized on H$_2$O - free basis

EXAMPLE 2

Formaldehyde (32.1 grams) and ammonia (12.2 grams) dissolved in water (55.7 grams) were reacted over HZSM-5 under the conditions specified in Example 1. The conversion of formaldehyde was 7.5 percent. Products were principally light gas, hydrocarbons, HCN and acetonitrile. Detailed product distribution is shown below:

TABLE II

| Products, wt. %$^a$ | |
|---|---|
| H$_2$, CO, CO$_2$ | 32.2 |
| HCN | 15.1 |
| Hydrocarbons | 26.8 |
| Acetonitrile | 25.9 |
| | 100.0 |

$^a$Normalized on H$_2$O - free basis.

EXAMPLE 3

Methanol (70 wt. percent) and ammonia (30 wt. percent) were reacted over HZSM-5 under the conditions specified in Example 1. The conversion of methanol was 95.7 percent. The products obtained were principally methylamines. Detailed product distribution is shown below:

TABLE III

| Products, wt %$^a$ | |
|---|---|
| Dimethylether | 2.9 |
| Hydrocarbons | 5.8 |
| Methylamines | 91.2 |
| Acetonitrile | 0.1 |
| | 100.0 |

$^a$Normalized on H$_2$O - free basis.

It will be seen from the above results of Tables I, II, and III that a mixture of products, including substantial amounts of nitriles and aminonitriles, was obtained by passing the three components, i.e., methanol, formaldehyde and ammonia over a crystalline aluminosilicate catalyst, such as ZSM-5. In the absence of either formaldehyde or methanol, a very different slate of products was obtained.

What is claimed is:

1. A method for synthesizing alkylnitriles and alkylaminonitriles which comprises effecting reaction between formaldehyde, C$_1$–C$_5$ monohydric alcohol and a compound having the formula R$_1$R$_2$NH where R$_1$ and R$_2$ are selected from the group consisting of hydrogen and alkyl groups containing 1 to 5 carbon atoms at a temperature between about 500° F. and about 1200° F., a pressure between about 1 and about 100 atmospheres and a liquid hourly space velocity between about 0.2 and about 20 in the presence of a catalyst comprising a crystalline aluminosilicate zeolite having a silica to alumina ratio of at least about 12 and a constraint index within the approximate range of 1 to 12 and recovering from the resulting reaction mixture, a product containing at least one of the above nitrile compounds.

2. The method of claim 1 wherein said nitrile compound is an alkylnitrile.

3. The method of claim 1 wherein said nitrile compound is an alkylaminonitrile.

4. The method of claim 2 wherein said alkylnitrile is CH$_3$CN, CH$_2$CH$_2$CN or mixtures thereof.

5. The method of claim 3 wherein said alkylaminonitrile is CH$_3$NHCH$_2$CN, CH$_3$NHCH$_2$CH$_2$CN, (CH$_3$)$_2$NCH$_2$CN or mixtures thereof.

6. The method of claim 1 wherein the reaction conditions include a temperature between about 700° F. and about 1000° F., a pressure between about 1 and about 100 atmospheres and a liquid hourly space velocity of between about 0.5 and about 10.

7. The method of claim 1 wherein the mole ratio of formaldehyde, C$_1$–C$_5$ alcohol and R$_1$R$_2$NH compound is $$1 \leq \frac{HCHO}{C_1\text{–}C_5 \text{ Alcohol}} \leq 5$$

$$1 \leq \frac{C_1\text{–}C_5 \text{ Alcohol}}{R_1R_2NH} \leq 10$$

8. The method of claim 1 wherein the mole ratio of formaldehyde, C$_1$–C$_5$ alcohol and R$_1$R$_2$NH compound is $$1 \leq \frac{HCHO}{C_1\text{–}C_5 \text{ Alcohol}} \leq 2$$

$$1 \leq \frac{C_1\text{–}C_5 \text{ Alcohol}}{R_1R_2NH} \leq 5$$

9. The method of claim 1 wherein said crystalline aluminosilicate zeolite is ZSM-5.

10. The method of claim 1 wherein said crystaline aluminosilicate zeolite is HZSM-5.

11. The method of claim 1 wherein said nitrile compound is CH$_3$CN, CH$_2$CH$_2$CN, CH$_3$NHCH$_2$CN, CH$_3$NHCH$_2$CH$_2$CN, (CH$_3$)$_2$NCH$_2$CN or mixtures thereof and said crystalline aluminosilicate zeolite is ZSM-5, ZSM-11, ZSM-12, ZSM-35 or ZSM-38.

12. The method of claim 1 wherein said alcohol is methanol and the R$_1$R$_2$NH compound is ammonia.

13. The method of claim 12 wherein said crystalline aluminosilicate zeolite is ZSM-5.

* * * * *